US011207687B2

United States Patent
Castell et al.

(10) Patent No.: US 11,207,687 B2
(45) Date of Patent: Dec. 28, 2021

(54) ARTIFICIAL CELLS

(71) Applicant: UNIVERSITY COLLEGE CARDIFF CONSULTANTS LTD, Cardiff (GB)

(72) Inventors: Oliver Castell, Cardiff (GB); David Barrow, Cardiff (GB); Divesh Baxani, Cardiff (GB)

(73) Assignee: UNIVERSITY COLLEGE CARDIFF CONSULTANTS LTD, Cardiff (GB)

(*) Notice: Subject to any disclaimer, the term of this patent is extended or adjusted under 35 U.S.C. 154(b) by 0 days.

(21) Appl. No.: 16/333,654

(22) PCT Filed: Sep. 15, 2017

(86) PCT No.: PCT/GB2017/052735
§ 371 (c)(1),
(2) Date: Mar. 15, 2019

(87) PCT Pub. No.: WO2018/051112
PCT Pub. Date: Mar. 22, 2018

(65) Prior Publication Data
US 2019/0255529 A1      Aug. 22, 2019

(30) Foreign Application Priority Data
Sep. 15, 2016 (GB) .................................. 1615741

(51) Int. Cl.
*A61K 9/107* (2006.01)
*B01L 3/00* (2006.01)
*G01N 33/543* (2006.01)

(52) U.S. Cl.
CPC ........ *B01L 3/502784* (2013.01); *A61K 9/107* (2013.01); *G01N 33/5432* (2013.01); *B01L 2200/0673* (2013.01)

(58) Field of Classification Search
None
See application file for complete search history.

(56) References Cited

U.S. PATENT DOCUMENTS

| | | | |
|---|---|---|---|
| 2002/0049276 A1* | 4/2002 | Zwick | C08L 53/02 524/476 |
| 2009/0170118 A1 | 7/2009 | Schmidt | |
| 2013/0129910 A1 | 5/2013 | Wallace | |
| 2014/0356289 A1 | 12/2014 | Bayley | |

FOREIGN PATENT DOCUMENTS

| | | | |
|---|---|---|---|
| EP | 0199362 | * 10/1986 | ............... A61K 9/50 |
| WO | WO 2013/064837 | * 5/2013 | ........... A61K 31/085 |
| WO | 2014/064444 | 5/2014 | |
| WO | 2016/009180 A1 | 1/2016 | |
| WO | 2017/004504 A1 | 1/2017 | |

OTHER PUBLICATIONS

Elani et al., Biochemical Society Transactions, Jun. 2016, vol. 44, part 3, pp. 723-730 (Year: 2016).*
Yasmann et al., Langmuir, 2015, vol. 31, pp. 350-357 (Year: 2015).*
Villar et al., (2013) Functional Droplet Interface Bilayers, In: Roberts G.C.K. (eds) Encyclopedia of Biophysics, Springer, Berlin, Heidelberg. Retrieved from the internet Oct. 5, 2020: file:///C:/Users/epyla/Downloads/Villar-Bayley2013_ReferenceWorkEntry_FunctionalDropletInterfaceBila%20(1).pdf (Year: 2013).*
Murua et al., Journal of Controlled Release vol. 132 (2008), pp. 76-83 (Year: 2008).*
Bayley et al., Droplet interface bilayers, Mol. Biosyst. Dec. 2008; 4(12): 1191-1208 (Year: 2008).*
International Search Report and Written Opinion for PCT/GB2017/052735.
Schlicht, B., et al., Droplet-interface-bilayer assays in microfluidic passive networks; Scientific Reports 5: 9951 Apr. 24, 2015.
Morgan, A.J., et al., Simple and Versatile 3D Printed Microfluidics Using Fused Filament Fabrication; PLOS ONE, vol. 11, No. 4, Apr. 6, 2016.
Baxani, et al., Bilayer Networks within a Hydrogel Shell: A Robust Chassis for Artificial Cells and a Platform for Membrane Studies; Angew. Chem. Int. Ed. 2016, 55, 14240-14245.
Elani, et al., Microfluidic generation of encapsulated droplet interface bilayer networks (multisomes) and their use as cell-like reactors; Chemical Communications; vol. 52. No. 35; Jan. 1, 2016; pp. 5961-5964.
Bayoumi, M., et al., Multi-compartment encapsulation of communicating droplets and droplet networks in hydrogel as a model for artificial cells; Scientific Reports | 7:45167 (2017).
United Kingdom IP Office Search Report dated May 31, 2017 for GB1615741.4.
Sarles, Stephen A., et al., Physical encapsulation of droplet interface bilayers for durable, portable biomolecular networks, Lab Chip, 2010, 10, 710-717.
Carreras, P., et al., A microfluidic platform for size-dependent generation of droplet interface bilayer networks on rails; Biomicrofluidics 9, 064121 (2015).
Nguyen, Mary-Anne, et al., Hydrodynamic trapping for rapid assembly and in situ electrical characterization of droplet interface bilayer arrays, Lab Chip, 2016, 16, 3576.
Venkatesan, Guru A., et al., Droplet immobilization within a polymeric organogel improves lipid bilayer durability and portability; Lab Chip, 2016, 16, 2116-2125.
Walsh, Edmond, et al., Formation of droplet interface bilayers in a Teflon tube; Sci. Reports, vol. 6, Sep. 29, 2016.

* cited by examiner

*Primary Examiner* — Scott Long
*Assistant Examiner* — Evelyn Y Pyla
(74) *Attorney, Agent, or Firm* — Stites & Harbison, PLLC; Patrick M. Torre

(57) ABSTRACT

The invention relates to an artificial cell system comprising at least one droplet-interface bilayer (DIB) encased within a shell; a suspension comprising same; and a method and a device for the manufacture of same.

10 Claims, 10 Drawing Sheets
(10 of 10 Drawing Sheet(s) Filed in Color)

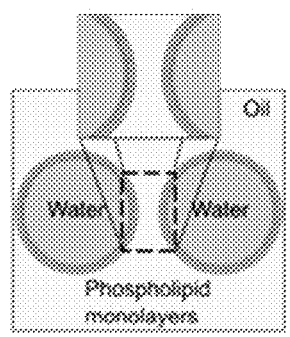
Figure 1A
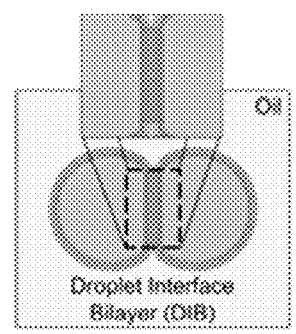
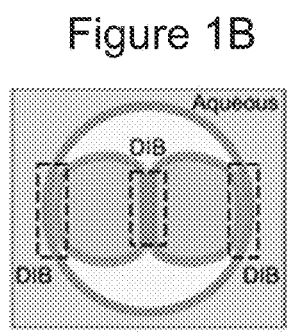
Figure 1B
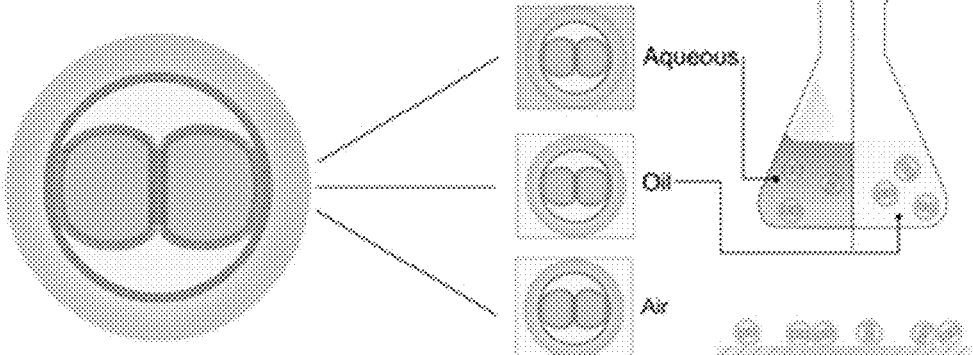
Figure 1C
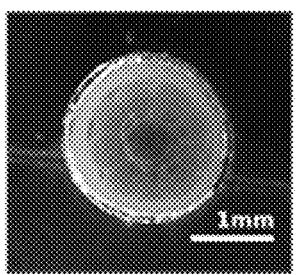
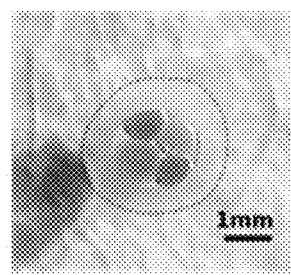
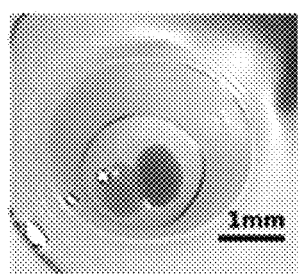
Figure 1D                Figure 1E                Figure 1F

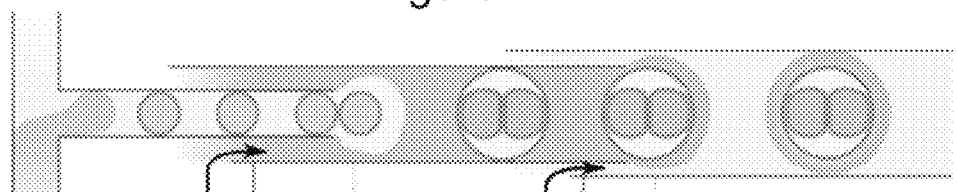
Figure 2A
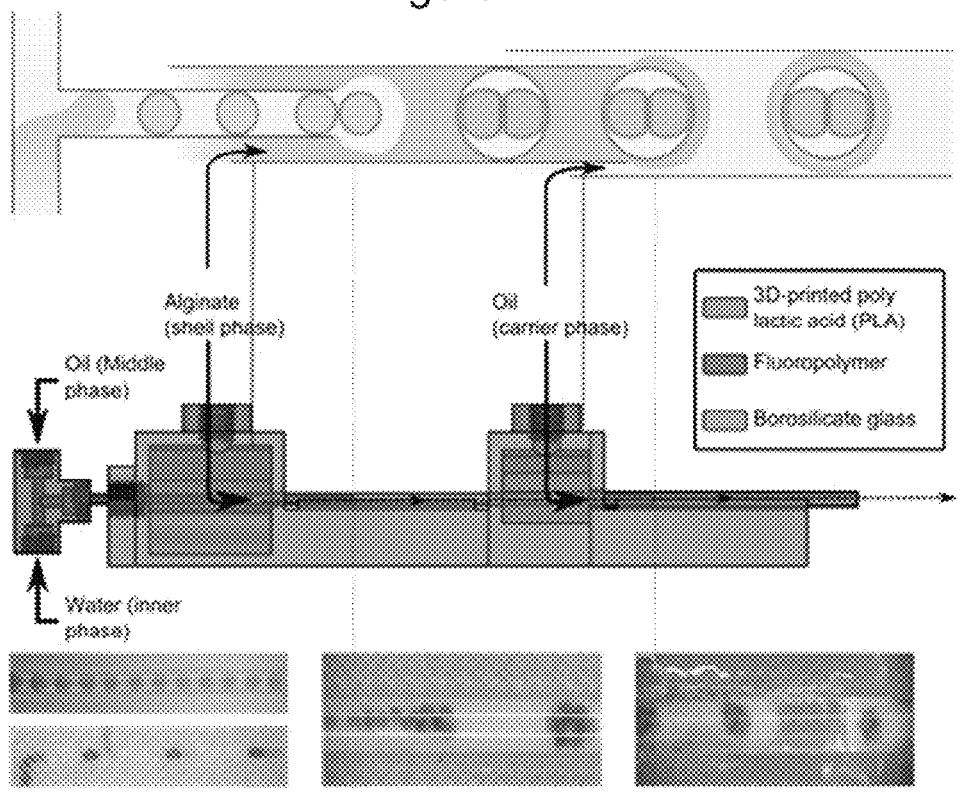
Figure 2B
Figure 2C    Figure 2D    Figure 2E

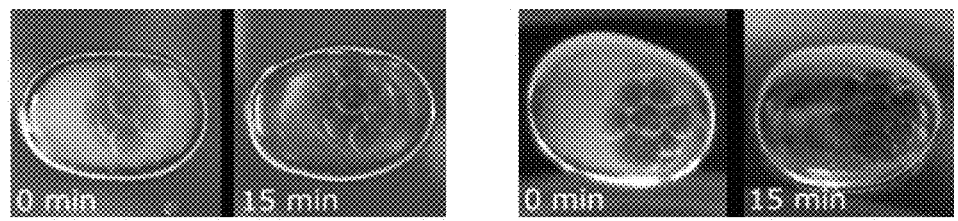
Figure 6
Figure 7A	Figure 7B
 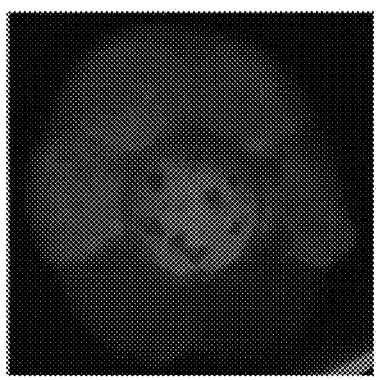
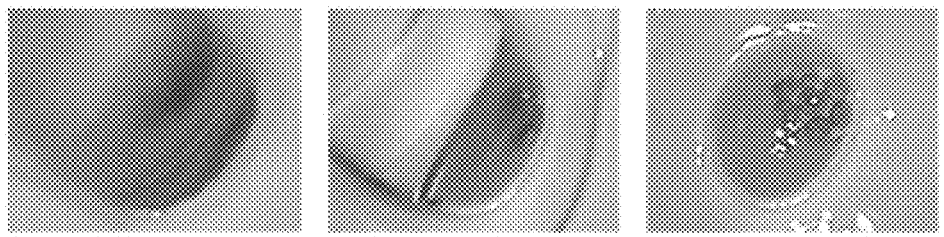
Figure 7C

ARTIFICIAL CELLS

This application is the national stage of international patent application no. PCT/GB2017/052735 filed on Sep. 15, 2017, which in turn claims priority from Great Britain Patent Application No. 1615741.4 filed on Sep. 15, 2016, the disclosures of which are incorporated herein by reference in their entirety.

TECHNICAL FIELD

The invention relates to an artificial cell system comprising at least one droplet-interface bilayer (DIB) contained within an oil droplet which is encased within a shell; a suspension comprising same; and a method and a device for the manufacture of same.

BACKGROUND

Lipid bilayers are an essential structural and functional component of biological cells. Approximately, 60% of current pharmaceuticals act on membrane targets with membrane proteins implicated in numerous diseases. As such, artificial bilayers are valuable tools for investigating lipid physical chemistry, membrane biophysics, membrane protein study and drug screening, as well as providing minimal models for the study of biological interactions, and more recently, forming the basis of artificial cells.

Conventional membrane models, such as planar lipid bilayers, giant unilamellar vesicles (GUVs) and black lipid membranes, have enabled studies including single channel electrophysiology, membrane imaging and combined measurements but measurements remain challenging due to a lack of stability, difficulty of formation, and limited throughput manufacture of model bilayer systems.

Droplet interface bilayers (DIBs) have more recently provided a simple alternative where lipid bilayers are formed through the contact of aqueous droplets in an oil environment in the presence of lipid. The practical advantages of DIBs have widened the scope of membrane study and application. The droplet based membrane compartmentalisation afforded by DIBs, has made them attractive tools for the development of functional bio-inspired devices, such as power-cells, synthetic tissue mimics, chemical logic platforms, and synthetic bioreactors as well as platforms for new single molecule studies in areas such as protein folding and DNA analysis. However, conventional DIBs are made in a continuum of oil and require anchorage either to a surface, an electrode/wire, constraint within a microfluidic channel or another supporting structure and consequently such constructs are not freestanding and are unable to interface with external aqueous environments. The potential use of such materials and their application to real world problems is thus severely limited by an inherent fragility. Further, current methods of manufacture are also tedious and manual.

We herein disclose the development of rugged, freestanding, mechanically stable artificial bilayer cells and systems comprised of droplets encased in a semi-permeable environment or shell (FIG. 1c). We show that such constructs are stable in air, water and oil environments, and readily tolerate mechanical manipulation, storage and manual handling; for example, by pipetting, tweezing, or manipulation by hand. The solid nature of the constructs allows for ease of storage and transport without a requirement for a specific media. Further, these novel constructs can be produced by carefully controllable automated methods that provide reliable control over the number of internal droplets and their composition. Importantly, these constructs retain the ability to communicate with the outside world through incorporation of membrane proteins, and their production can be readily automated and scaled. They also represent a robust mimic of the cell membrane paving the way for the practical application of these artificial membranes or droplet networks in diverse areas such as medical applications, drug testing, biophysical studies and their use as synthetic cells. Additionally, the ability of the described constructs to spatially segregate chemical reagents, biological molecules and other active or functional materials makes such constructs highly useful candidate chassis for "artificial cells" and functional soft-matter devices which may find applications in diverse spheres such as smart drug delivery, environmental monitoring, lab-in-a-capsule applications, synthetic biology fields, drug screening, light energy harvesting or synthetic photosynthesis, molecular evolution and bioresponsive smart materials.

SUMMARY

According to a first aspect of the invention there is provided an artificial cell system comprising: at least one hydrophilic/polar droplet constrained within an amphiphilic monolayer and contained within an oil droplet to provide at least one droplet-interface bilayer (DIB) which is encased within a shell wherein said shell is at least semi-rigid.

Reference herein to a shell is to a casing, also referred to herein as an outerphase, that covers or contains said oil droplet in which said DIB is formed. In the instance where said shell is permeable or semipermeable said shell covers or contains said oil droplet in which said DIB is formed to such an extent that the contents of said shell are retained by same, in this way the contents of said shell can communicate with the external environment but are help together within the shell.

Those skilled in the art will appreciate that reference herein to a DIB is to, ideally, an aqueous droplet in oil in the presence of amphiphile, typically but not exclusively lipid, that spontaneously self-assembles to form a lipid monolayer surrounding said droplet and when one such droplet is brought into contact with a further amphiphile/lipid monolayer, for example provided by said oil droplet in which it is contained, a droplet-interface bilayer (DIB) forms; or when two such droplets are brought into contact with each other, since both are contained within the oil droplet, a droplet-interface bilayer (DIB) forms.

In a preferred embodiment of the invention, typically the amphiphilic monolayer comprises lipid molecules which are usually, but not necessarily, provided in an oil-lipid mixture. The lipid can be a naturally occurring lipid to mimic natural systems or a synthetic lipid with a view to creating artificial membranes. Alternatively, the amphiphilic monolayer comprises an amphiphilic polymer, fatty acid or, indeed, any other available amphiphile. Typically the aqueous droplet can be water or a water-based liquid or gel or a polar liquid or gel.

The lipid molecules may be any of the major classes of lipid, including fatty acyls, glycerolipids, glycerophospholipids, sphingolipids, sterol lipids, prenol lipids, saccharolipids and polyketides. Notable examples include a phospholipid, a glycolipid or cholesterol. However, the invention extends to any amphipathic molecules capable of forming a bilayer.

The amphipathic molecules need not be all of the same type. The amphipathic molecules may be mixtures for example the amphipathic molecules brought into contact may be of different types and so give rise to a bilayer formed of two different monolayers; thus being asymmetric.

More specifically the invention provides: an innerphase having at least one hydrophilic/polar droplet constrained in a amphiphilic monolayer and wherein said monolayer is in physical contact with at least one other amphiphilic monolayer provided either by at least one other hydrophilic/polar droplet constrained in a amphiphilic monolayer and/or the oil droplet to provide at least one DIB; and an outerphase encapsulating said innerphase, wherein said outerphase comprises a polymer forming at least a semi-rigid shell.

The hydrophilic/polar solution may be freely chosen for the experimental study which is to be performed. The hydrophilic/polar solution of each droplet may be the same or different. The nature and concentration of the solutes can be freely varied to vary the properties of the solution for example the pH can be varied over a wide range. In experiments using electrical measurements the charge may vary; also the osmolarity may vary. The hydrophilic/polar solution may be, for example, water, hydrogel, polymer, alcohol or fluorinated liquid.

The hydrophobic medium can also be selected from a wide range of materials. The material is hydrophobic so that the aqueous solution forms a droplet rather than mixing with the hydrophobic medium but otherwise the hydrophobic medium can be freely chosen. The viscosity of the hydrophobic medium can be selected to affect the movement of the droplets and the speed of formation of the layer of amphipathic molecules.

The hydrophobic medium may be an oil. Any type of oil is suitable as long as its surface activity is relatively high, and that it does not destabilize the formed bilayers. The oil may be a hydrocarbon which may be branched or unbranched, for example a hydrocarbon having from 5 to 20 carbon atoms (although hydrocarbons of lower molecule weight would require control of evaporation). Suitable examples include alkanes or alkenes, such as hexadecane, decane, pentane or squalene. Other types of oil are possible. For example the oil may be a silicone oil, fluorocarbon or a partially fluorinated hydrocarbon. This might be useful for the study of some systems, for example to minimise loss of a particular membrane protein or analyte from the droplet or to control gas content such as oxygen.

In a preferred embodiment, each droplet may be of the same type. Alternatively, each hydrophilic/polar droplet may be of a different type.

Yet more preferably still, said DIB may be engineered to further comprise additional constituents such as, but not limited to, membrane protein, solution protein, peptide, DNA, RNA, cells, polymers, biological molecules, liquid crystals, organic and inorganic molecules, and nanoparticles. Yet more preferably said DIB may comprise more than one of the afore and in some instances a number of components of a known biological pathway or a synthetic pathway.

In a preferred embodiment of the first aspect of the invention, said shell is at least semi-permeable, so as to permit communication of the DIB cell system with its external environment. Ideally said semi-permeability is via transport pathways known to those skilled in the field such as, but not limited to, diffusion or active transport. In this manner, the artificial cell system can interact with the surrounding environment. Alternatively, said shell is non-permeable permitting isolation and/or storage of the artificial cell system.

Preferably said innerphase contains polar droplets of 10 nm-1 cm diameter, most preferable 1 um-1 mm and said outerphase shell has a compatible geometry.

More preferably, said shell is characterized by a porosity of between 0-99% and every integer there between, or more ideally 10-99%, or more ideally still selected from the group comprising or consisting of: 10%, 20%, 30%, 40%, 50%, 60%, 70%, 80%, 90%, 95% or any 1% or 0.1% integer there between.

As is known to those skilled in the art, reference herein to porosity, or void fraction, is a measure of the void (i.e. "empty") spaces in a material, and is a fraction of the volume of voids over the total volume, between 0 and 1, or as a percentage between 0 and 100%.

Alternatively, or additionally, the permeability of said shell is characterized by a mesh density of between 0.1 nm.-1,000,000 nm and every 0.1 nm integer there between, or more ideally 1-10,000 nm, or more ideally still selected from the group comprising or consisting of: 10, 100, 1000 nm, or any 0.1 nm there between.

In yet a further preferred embodiment, said shell is characterized by an average pore size of between 0.1-100, 000 nm. More preferably, said pore size is between 0.1 μm to 1000 μm, yet more preferably 1 μm and 500 μm. Most ideally the pore size is selected from the group comprising or consisting between 10 and 100 μm or any 0.1 μm there between. By controlling the size of the pores, in addition to overall porosity, the user is able to control the permeability of the shell, for example, to exclude diffusion of protein, or certain types, but maintain aqueous diffusion and transfer of small solutes. An additional example where the user is able/desires to control the permeability of the shell is where it is desirable to prohibit cellular access e.g. in applications wherein it is desired to evade immune system responses, thus pore size/porosity would be selected with this in mind. A further example where the user is able/desires to control the permeability of the shell is where it is desirable to prohibit cellular access e.g. in applications wherein it is desired to control ion flux, thus pore size/porosity would be selected with this in mind.

As will be appreciated by those skilled in the art, when comprising pores, the shell will also comprise structure defining those pores, which may be viewed as interconnections between the pores. In such an embodiment the surface area of the structure may be of comparable size to the surface area of the pores or even smaller. By controlling the size of the pores and the surrounding structure the user is able to control the permeability of the shell, for example, to exclude diffusion of protein, of certain types, but maintain aqueous diffusion and transfer of small solutes.

As will also be appreciated by those skilled in the art, in the instance where the shell is a hydrogel, or similar structure, it will contain a number of collapse features also known to the skilled man as 'pores', only some of which, via connecting with other neighboring pores, will connect the inside of the shell with the outside environment. Nevertheless, the average pore size will represent a measure of the porosity or permeability of the shell.

In order to tolerate mechanical manipulation, storage and manual handling of the artificial cell system, it is necessary for the shell to have certain mechanical properties. As will be appreciated by those skilled in the art, mechanical strength of a material can be defined in terms of numerous parameters. In a preferred embodiment, said shell has a mechanical strength characterized by a compressive modulus of between 0.0001-500 GPa and every integer there between, or more ideally 0.1-50 GPa, or more ideally still selected from the group comprising or consisting of: 1 GPa, 2.5 GPa, 10 GPa or any 0.1 GPa there between.

Alternatively, or additionally, the said shell is characterized by a Young's modulus of between 0.1-10000 KPa and every 0.1 KPa integer there between, or more ideally 1-500 KPa, or more ideally still selected from the group comprising or consisting of: 5, 25, 75 KPa, or any 0.1 KPa there between.

It has been found that the viscosity of the shell is important for manufacturability prior to gelling when the shell transitions from a liquid to a (semi)-solid state. Accordingly, in yet a further preferred embodiment, said shell is characterized by a viscosity of between 0.00001-10000 cP and every 0.1 cP integer there between, or more ideally 0.1-1000 cP, or more ideally still selected from the group comprising or consisting of: 1, 10, 200 cP, or any 0.1 cP there between.

In yet a further preferred embodiment, said shell is manufactured from a polymer characterized by an acid dissociation constant pKa value of between 0-14 and every 0.1 integer there between, or more ideally 2-7, or more ideally still selected from the group comprising or consisting of: 2.5, 3.5, 4.5, or any 0.1 there between. It has been found that there is a correlation between the pKa value and gelling of the shell, and thus its ability to form at least a semi-rigid structure.

In yet a further preferred embodiment of the invention said shell is hydrophilic. As will be appreciated by those skilled in the art, in this manner an aqueous environmental compatibility is imparted on the cell system.

Alternatively, the shell may not be hydrophilic and the lipid monolayer may be formed by the attachment of lipid or lipid-like molecules to the surface.

The shell, ideally hydrated shell, may be of any thickness, preferably from about 1 nm to about 10 cm, more preferably from about 0.1 μm to about 1 cm, most preferably from about 10 μm to about 1 mm.

In yet a further preferred embodiment still, said shell has a transparency of at least 1%, or more ideally at least 50%, or most ideally at least 80%. The requirement for and degree of transparency will vary according to the nature of the application, such as for example, wherein a visual readout such as colour or fluorescence is to be observed transparency is favoured, transparency is also favoured where the use/administration of light within the cells is required to activate photoactivatable contents.

In yet a further preferred embodiment, said shell is comprised of a polymer wherein said polymer is capable, under suitable conditions, of undergoing depolymerisation. For example, Alginate polymers can be depolymerised with microwave irradiation or more usually by competitive calcium chelation (for example with EDTA). The ability to trigger depolymerisation of the shell and revert it to a liquid/fluid/un-encased state may be desirable for certain applications.

In yet a further preferred embodiment of the invention, said shell further comprises at least one environmentally responsive element or material whereby a change in the properties of the shell can be induced by application of an appropriate stimuli to the shell such as, but not limited to temperature dependent swelling or contraction, solvation dependent swelling or contraction or photosensitive polymerization.

In certain embodiments the shell structure may be made rigid by cross-linking same or the self-adherence of same. Preferably the cross-linking or self-adherence is controlled by the user either immediately before, during or after formation of the shell structure around the internal contents.

In yet a further preferred embodiment still, said polymer is a hydrogel.

Reference herein to a hydrogel refers to a network of polymer chains that are hydrophilic, sometimes found as a colloidal gel in which water is the dispersion medium. Hydrogels are highly absorbent (they can contain over 90% water) natural or synthetic polymeric networks. Hydrogels also possess a degree of flexibility very similar to natural tissue, due to their significant water content. Preferably said hydrogel is in a solid or semi-solid phase.

According to this further preferred embodiment wherein said shell is a hydrogel, the shell may be composed of between 0.01 and 90% polymer, preferably between 0.1 and 10% polymer and more preferably between 0.5 and 5% polymer content.

The terms "solid" and "semi-solid" as used herein are understood to have their ordinary meaning to a person skilled in the art. Essentially the term "solid" refers to a substrate that is rigid and resistant to deformation, and "semi-solid" refers to a substrate that has properties between those of a solid and a liquid. Preferably a semi-solid substrate has some degree of flexibility but is rigid enough to maintain its shape. This latter feature is advantageous because once completely surrounding its encapsulated contents, it will not immediately conform to the shape of any containing container or immediately deform due to gravitational or surface forces when contacting a gas, liquid or solid, or moving between environments. An example of a semi-rigid or semi-solid shell is a gel.

Most preferably said hydrogel is selected from the group comprising agarose, chitosan and alginate.

Alternatively, said polymer is polyacrylamide, polyethylene glycol, nitro-cellulose, polycarbonate, aerogel, cellulose acetate, anodisc material, polyethersulphone, naphion, nylon or porous silica.

As mentioned, said DIB may be engineered to further comprise additional constituents such as at least one or more protein(s). Proteins may be constituted into the droplet interface bilayers providing one way in which material and/or information may be transferred between the internal droplets and the outer shell; the latter itself being communicable with the external environment.

In a preferred embodiment, the protein is a membrane-associated protein which is anchored directly or indirectly to the bilayer. The protein may be a selective or non-selective membrane transport protein, an ion channel, a pore forming protein or a membrane-resident receptor.

Preferably the membrane-associated proteins diffuse into and/or associate with the bilayer causing a detectable change in at least one property of the bilayer; this change in property may be physical, optical, electrical or biochemical.

Whilst the invention concerns at least one DIB within a shell, the invention extends to the provisions of multiple DIBs within multiple shells, ideally, where each DIB is engineered by way of its content, typically protein content, to perform a first test and subsequent DIBs are engineered to perform a further test that, ideally, corroborates, validates or provides further information having regard to the nature of the interrogation performed when said first test is undertaken. So, for example said first test undertaken by a first DIB (engineered to undertake this first test) may provide a result/signal indicating a membrane protein is inactivated and a second test undertaken by a second DIB (engineered to undertake this second test) may provide a result/signal indicating how the membrane protein is inactivated. Those skilled in the art will appreciate the complexity of the artificial cell system and the nature of the tests that can be undertaken using same are almost limitless once one is able to provide encased DIBs.

Accordingly the invention, in a second aspect, also provides a liquid suspension comprising a liquid in which there is provided a plurality of artificial cell systems wherein each artificial cell system comprises: at least one hydrophilic/polar droplet constrained within a lipid monolayer and contained within an oil droplet to provide at least one droplet-interface bilayer (DIB) which is encased within a shell wherein said shell is at least semi-rigid.

Most preferably, said suspension comprises a plurality of artificial cell systems wherein at least one cell system is different from the others or where each cell system is different the others.

A further possibility, as an extension to those described above, is to form lines or series of cell systems where bilayers are formed between adjacent shells, such that higher order bilayer networks can be built with self-contained internal DIB networks within the shell of each unit of the higher order network. Such internal networks could be isolated from, or in communication with the higher order network within which they are contained, even communicating with other internal networks via the wider, higher order, network. Such a configuration is expected to generate significant complexity for interesting, useful and unique experiments. For example, this may include formation of 2D and 3D structures comprising eDIBs, alone or in combination with other materials such as cell/tissue scaffolds.

According to a third aspect of the invention, there is provided a method for manufacturing an artificial cell system as described herein comprising the microfluidic mixing of at least two hydrophilic/polar liquids and at least one hydrophobic liquid.

In a preferred method of the invention we have encased DIBs by coaxially flowing within channels said liquids. Most preferably we flow a first hydrophilic liquid and a first hydrophobic liquid together to form droplets. We then manipulate the flow kinetics to bring droplets together to form DIBs and then we flow this heterogenous fluid comprising droplets within a further liquid, which has been selected to form the outer shell. This outer shell is formed into a casing, typically a droplet then, most preferably, and if required, we change conditions so that the outer shell hardens. This can be done by changing a physical property such as temperature, pH or the like or by exposing the system to a hardening agent such as calcium—in the case of certain hydrogels. Finally, we flow the shell encased DIBs into a further liquid that is selected to provide the suspension in which the shell encased DIBs exist.

If this liquid is non-miscible with the liquid shell phase the hardening described afore can be delayed until this later suspension has been formed. Subsequently, we place the shell encased DIBs in a chosen environment of operation for testing, if required.

Ideally, said channels are of a selective wettability to allow for the high-throughput generation of droplets in a carrier.

By selecting the number and nature of liquids and channels and their interrelationship we are able to produce a monophase (monodisperse emulsions) as well as hierarchical arrangements of droplets within droplets (double & triple emulsions) each of a defined composition.

Thus ideally the method of the invention involves the use of sequential coaxial flow geometries and, following the initial T-junction mixing of the DIB creating liquids, the alternate use of hydrophilic and hydrophobic liquids.

More specifically, where arrangements of droplets with different chemical identity are to be generated within a shell or a number of different shells the method involves the use of multiple T-junction mixing followed by coaxial flow mixing and then convergent mixing, thus enabling the generation of DIB droplets of different compositions, their encasement within shells, which can be of different compositions, and their subsequent suspension in a common fluid.

Moreover, a selected one or more of said liquids is provided with a least one membrane protein or protein to be tested or means, such as components, to generate said protein.

Whilst the method of manufacture has been disclosed having regard to microfluidic arrangements alternative arrangements may be employed and it is expected other manual or automated methods of production may also be used.

However, advantageously, the microfluidic manufacture techniques involved in the generation of shell encased DIBs allows for high-throughput production and control over the volume of the individual compartments. Internal aqueous droplets of differing contents are also possible with microfluidic devices and allow for non-equilibrium reactions to occur across the different compartments.

According to a fourth aspect of the invention, there is provided a device for manufacturing an artificial cell system as described herein comprising at least one droplet generating junction for mixing a first hydrophilic/polar liquid and a first hydrophobic liquid and wherein said junction terminates within a coaxially aligned channel, which in turn terminates within another downstream coaxially aligned channel for the subsequent mixing of at least one further hydrophilic liquid and at least one further hydrophobic liquid.

Reference herein to a coaxially aligned channel is to a channel whose central axis is aligned with that of the central axis of a neighboring channel. Where droplet generation is required adjacent channels are further arranged so that one microfluidic channel terminates, ideally centrally, within another.

In a preferred embodiment said droplet generating junction is selected from the group comprising: a t-junction, x-junction, y-junction, coaxial junction, constriction junction, or batwing junction.

In yet a further preferred embodiment said at least one channel is either a linear channel or selected from the group comprising: a t-junction, x-junction, y-junction coaxial junction, constriction junction, or batwing junction.

More preferably said device comprises a plurality of droplet generating junctions through which the liquids in the system flow. Ideally different liquids are mixed in the different droplet generating junctions. Yet more preferably each droplet generating junction is connected to at least one coaxially aligned flow channel which ideally, where droplets are to be made, terminates centrally within a further coaxially aligned channel. Yet more preferably still at least two of said flow channels converge.

More preferably still said device comprises at least one droplet generating junction having a plurality of said coaxially aligned channels at least one of which terminates centrally within a further coaxially aligned channel.

Yet more preferably each droplet generating junction comprises a plurality of said co axially aligned channels.

Yet more preferably selected ones of said coaxial flow channels converge.

Throughout the description and claims of this specification, the words "comprise" and "contain" and variations of the words, for example "comprising" and "comprises", mean "including but not limited to" and do not exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

All references, including any patent or patent application, cited in this specification are hereby incorporated by reference. No admission is made that any reference constitutes prior art. Further, no admission is made that any of the prior art constitutes part of the common general knowledge in the art.

Preferred features of each aspect of the invention may be as described in connection with any of the other aspects.

Other features of the present invention will become apparent from the following examples. Generally speaking, the invention extends to any novel one, or any novel combination, of the features disclosed in this specification (including the accompanying claims and drawings). Thus, features, integers, characteristics, compounds or chemical moieties described in conjunction with a particular aspect, embodiment or example of the invention are to be understood to be applicable to any other aspect, embodiment or example described herein, unless incompatible therewith.

Moreover, unless stated otherwise, any feature disclosed herein may be replaced by an alternative feature serving the same or a similar purpose.

BRIEF DESCRIPTION OF THE DRAWING FIGURES

The patent or application file contains at least one drawing executed in color. Copies of this patent or patent application publication with color drawing(s) will be provided by the Office upon request and payment of the necessary fee.

The Invention will now be described by way of example only with reference to the Examples below and to the following Figures wherein:

FIG. 1A illustrates the formation of droplet interface bilayers (DIBs) from the contact of two droplets of water in oil in the presence of lipid.

FIG. 1B shows formation of DIBs within a droplet of oil.

FIG. 1C shows encapsulation of a droplet of oil containing DIBs in an alginate shell creates a robust freestanding structure compatible and communicable with a range of environments.

FIG. 1D is an image of encased DIBs (eDIBs) prepared in the laboratory with multiple internal aqueous cores.

FIG. 1E is an image of eDIBs prepared in the laboratory with another differing number and differing identity of internal aqueous cores.

FIG. 1F is an image of eDIBs prepared in the laboratory with yet another differing number and differing identity of internal aqueous cores.

FIG. 2A depicts the double coaxial microfluidic concept employed for the formation of eDIBs.

FIG. 2B is a side-view CAD schematic of the microfluidic device.

FIG. 2C shows images of each successive droplet generation process, specifically showing creation of aqueous droplets in oil.

FIG. 2D shows segmentation of the oil phase of FIG. 2C within a continuous alginate flow to create discrete oil droplets containing aqueous droplet networks.

FIG. 2E shows subsequent segmentation of the alginate flow of FIG. 2D to encase these constructs in an alginate shell (eDIBs). Aqueous droplets can be formed by a single (FIG. 2C, upper panel) or double (FIG. 2C, lower panel) T-junction geometry to define the internal contents of the aqueous droplets.

Figure 3:
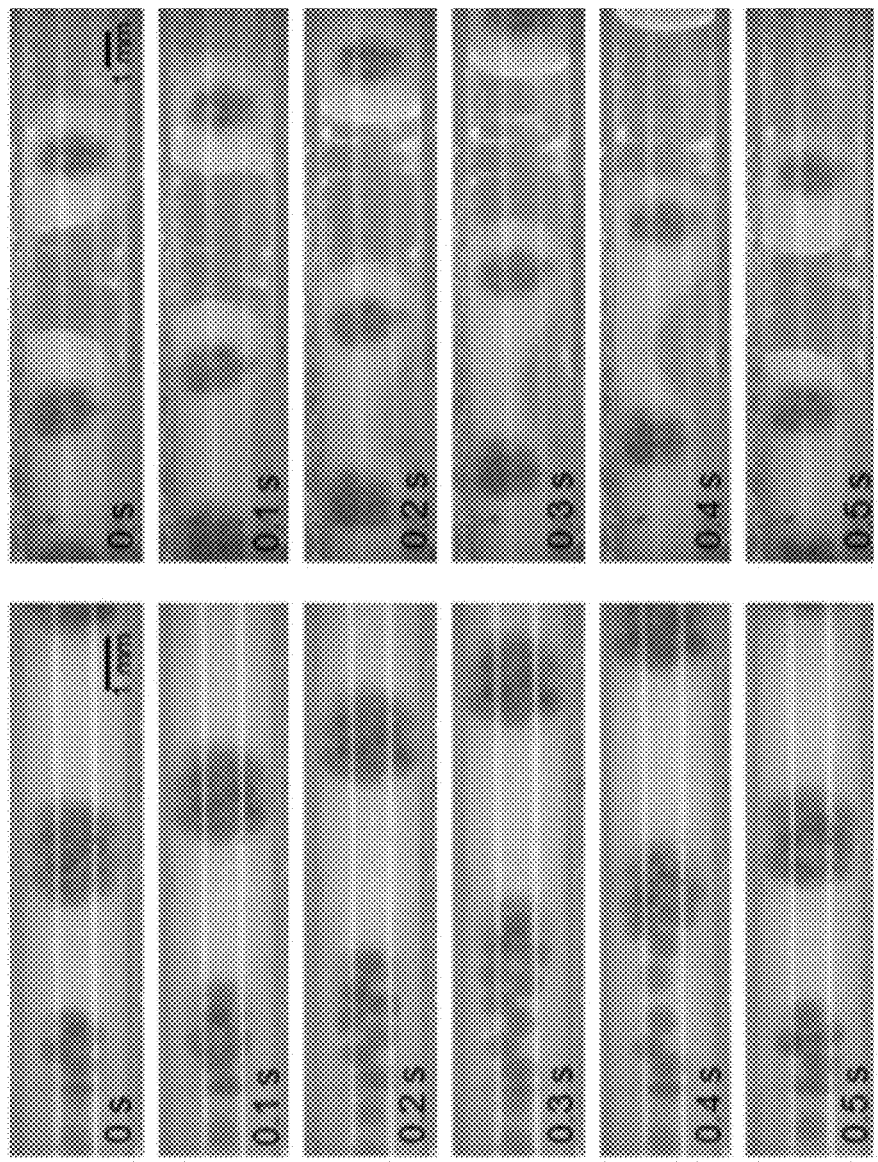
Figure 4E:
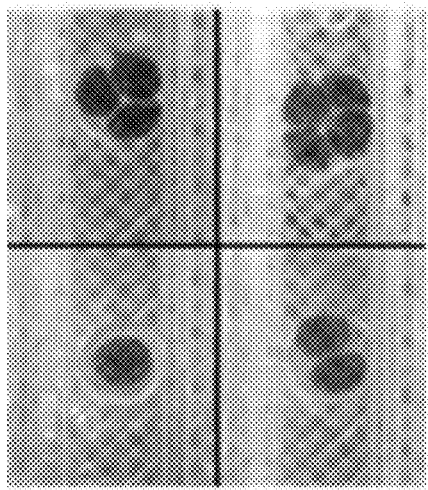
Figure 4F:
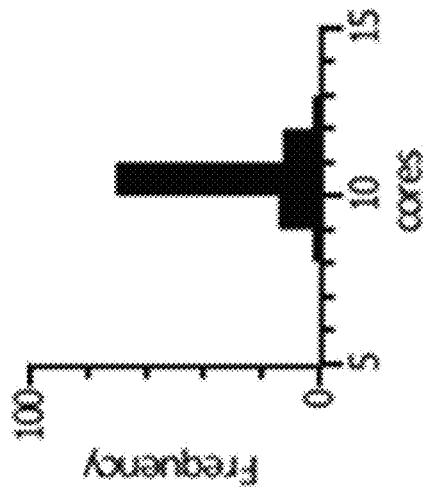
Figure 4B:
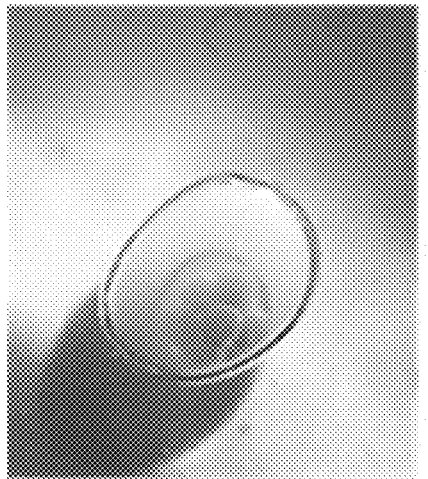
Figure 4D:
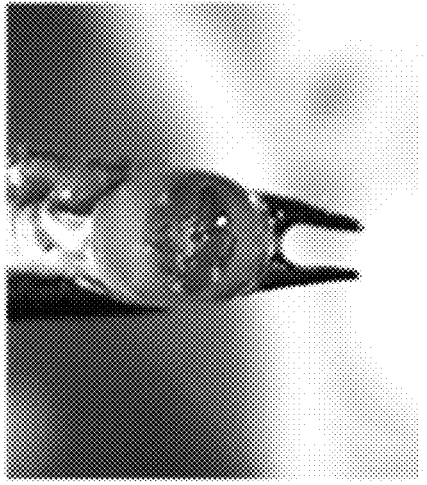
Figure 4A:
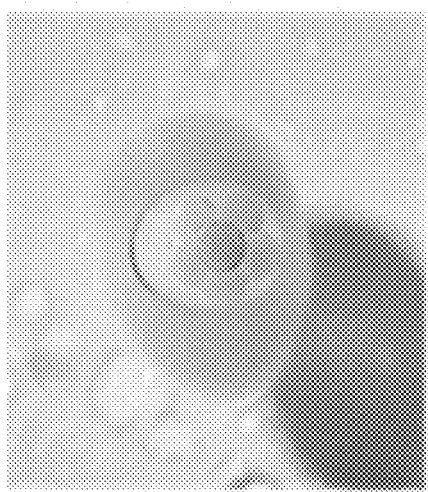

FIG. 3. Time sequence images of the microfluidic manufacture of eDIBs. Double emulsions (left) are formed of aqueous droplets creating a DIB network within an oil droplet in a continuous alginate flow. At the second coaxial flow geometry, a triple emulsion is formed (right) creating an alginate shell around the bilayer construct (eDIB). Experimental flow rates: 0.196:0.196:2.5:6.67 ml min$^{-1}$ (aqueous, oil, alginate, oil);

FIG. 4A shows compatibility of encased droplet interface bilayers (eDIBs) with an aqueous environment.

FIG. 4B shows compatibility of encased droplet interface bilayers (eDIBs) with a mineral oil aqueous environment.

Figure 4C:
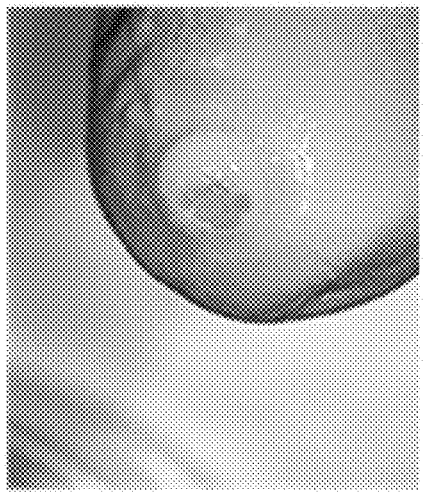

FIG. 4C shows an eDIB placed on a gloved finger and exposed to the air.

FIG. 4D shows an eDIB manipulated with tweezers.

FIG. 4E shows an image of an eDIB demonstrating the formation of oil droplets with one, two, three and four internal aqueous cores.

FIG. 4F is a histogram showing the reproducibility of production of constructs with higher numbers of internal cores (~10) (internal aqueous phase: 0.196 ml min-1; internal oil phase: 0.196 ml min-1; alginate phase: 2.5 ml min-1; carrier oil phase: 6.67 ml min-1, scale bars: 1 mm).

Figure 5A:
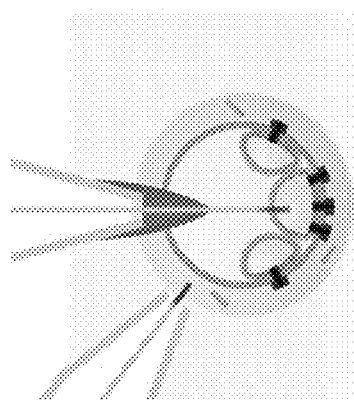

FIG. 5A is an image of an eDIB with Ag/AgCl electrodes in the alginate shell and in an internal aqueous phase (top panel). In response to a ±23 mV triangle wave, a capacitive current is measured, signifying the presence of a lipid bilayer (bottom panel).

Figure 5B:
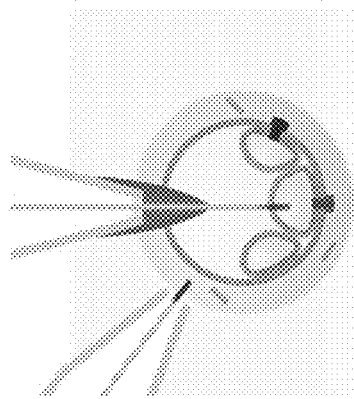

FIG. 5B shows that a short period of electroporation in an eDIB membrane is observed during a period under an applied potential of +50 mV.

Figure 5C:
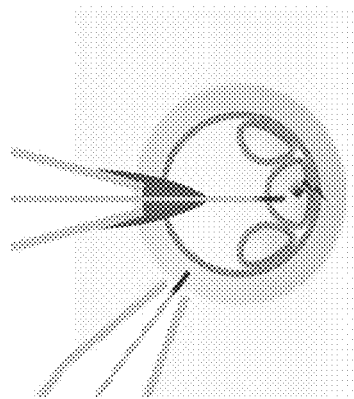

FIG. 5C shows that following the contacting of the external shell of an eDIB with an aqueous droplet containing the protein pore, α-Hemolysin, protein insertion events are detected facilitating ion flux across the bilayer (red traces). Transient current spikes are also observed (blue traces) due to protein insertion into neighboring bilayers of the droplet bilayer network of the eDIB.

Figure 5D:
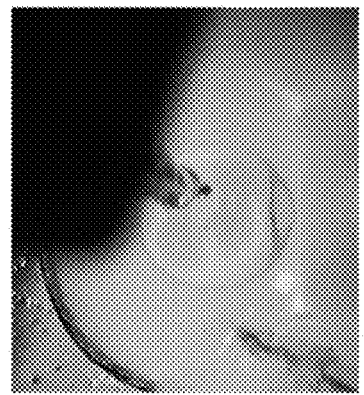

FIG. 5D shows that at higher protein concentrations successive step-wise increases in current are measured as multiple protein pores insert (step size ~18 pA), with both direct (c red) and indirect (c blue) protein insertions measured.

FIG. 6. The outer shell of a single eDIB becomes transparent over a period of approximately 15 minutes. The alginate shell of eDIBs becomes transparent as partitioning of acetic acid from the carrier oil phase causes a reduction in pH reacting with the particulate CaCO3 producing soluble calcium and carbon dioxide. The removal of suspended calcium carbonate results in transparency of the eDIB shell. Here, alginate phase contains 2% (w/v) low viscosity alginate and 75 mg/mL CaCO3. In accordance with the gelling mechanism transparency is realised more rapidly at the core perimeter as acetic acid-partitions into the shell from the external oil phase;

FIG. 7A shows eDIBs stored in aqueous solution in a sample tube 11 days after preparation. The alginate shell of the constructs is not readily visible owing to complete dissolution of calcium carbonate and equilibration with the external environment.

FIG. 7B is a fluorescent microcopy image of eDIB construct with internal cores containing 50 μM sulphorhodamine B. eDIBs were pipetted onto microscope slides for imaging. The image was acquired with a custom-built epifluorescence microscope with a 4× objective and using a 532 nm laser illumination.

Figure 8:
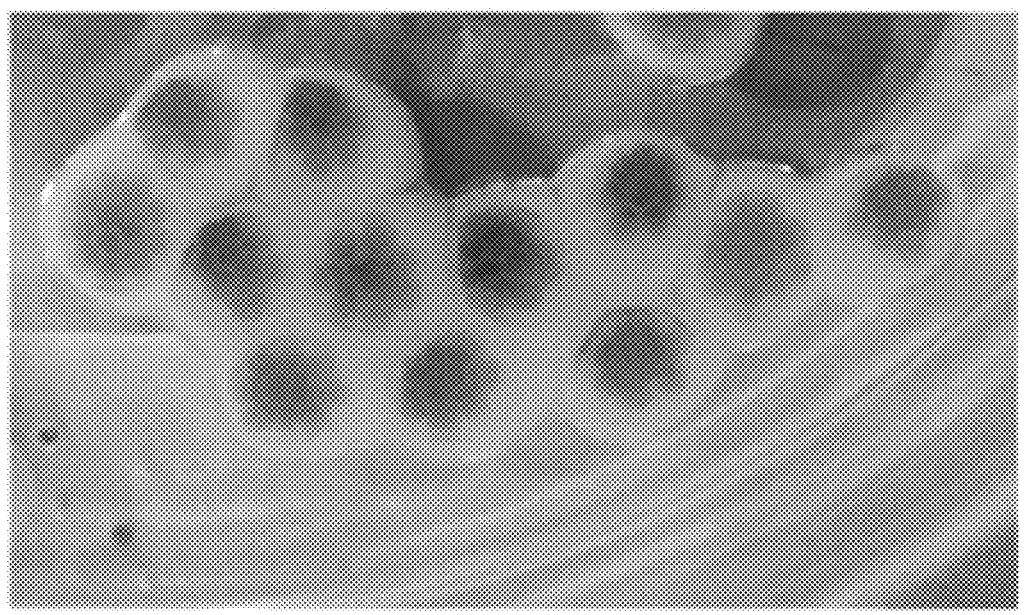
Figure 9A:

FIG. 7C shows a sequence of images demonstrating the pipetting of eDIBs from an oil solution onto the surface of a polymer Petri dish;

FIG. 8 shows an image of 12 encapsulated DIBs in hydrogel shells forming one single unit or a "proto-tissue";

FIG. 9A shows eDIBs in the exit tube of the microfluidic device.

Figure 9B:
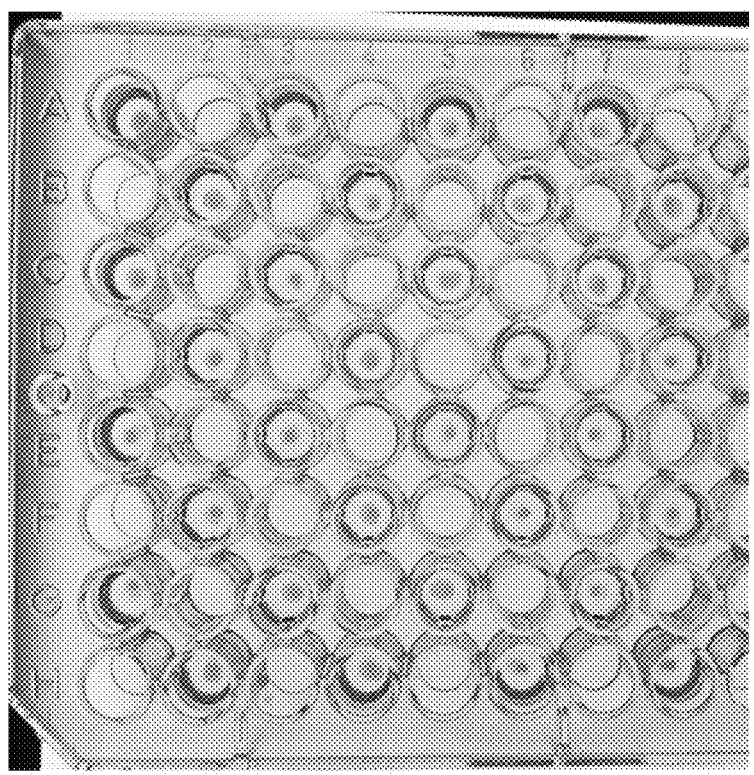

FIG. 9B shows eDIBs placed in wells of a 96 well plate. The microfluidic production of eDIBs means they can easily be placed directly in defined locations, such as individual wells of a multi-well plate, either manually or by automated means.

Figure 10A:
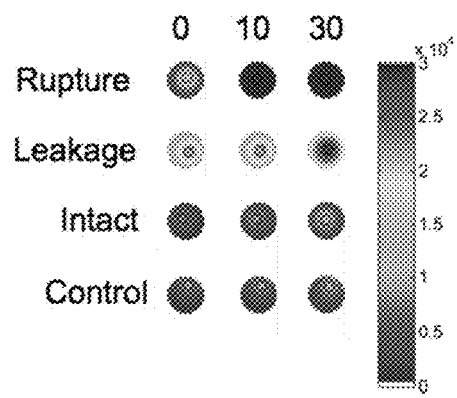

FIG. 10A shows fluorescent measurements of individual eDIBs in a 96 well plate. In this demonstration calcein leakage is used to report on membrane integrity. Intact, ruptured or pore formation can be determined, each with characteristic spatial and temporal fluorescent profile and magnitude.

Figure 10B:
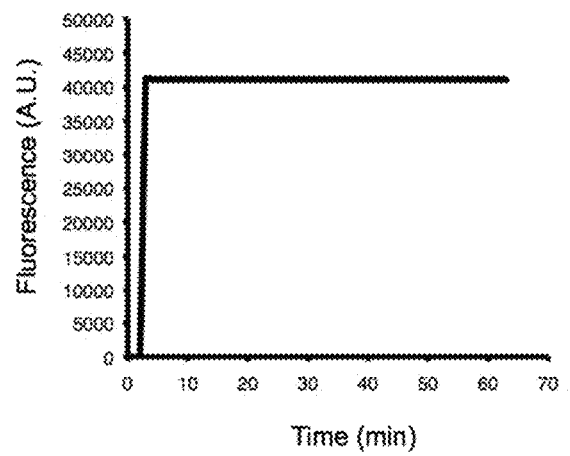

FIG. 10B shows fluorescent measurement of membrane rupture on addition of detergent.

Figure 10C:
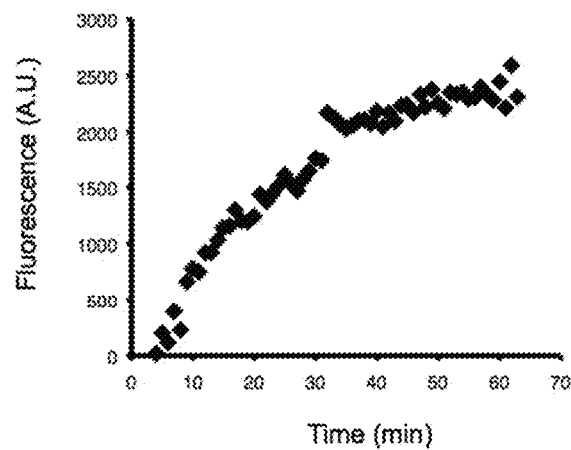
Figure 10D:
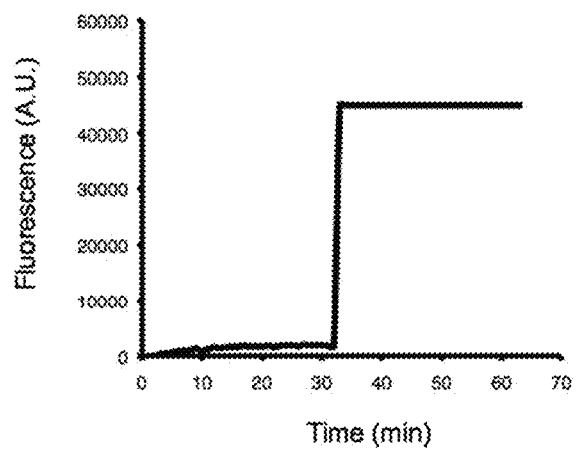

FIG. 10C shows calcein leakage as a result of pore formation on the addition of low concentration of detergent FIG. 10D shows measurement of pore formation followed by bilayer rupture.

Figure 11A:
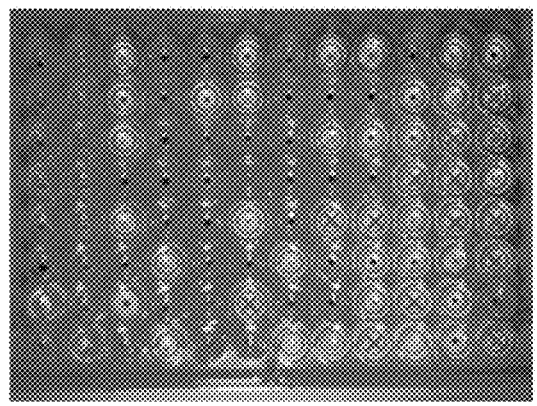

FIG. 11A shows high density optical screening of eDIBs in 96 well plate offering single bilayer measurement resolution with high throughput.

Figure 11B:
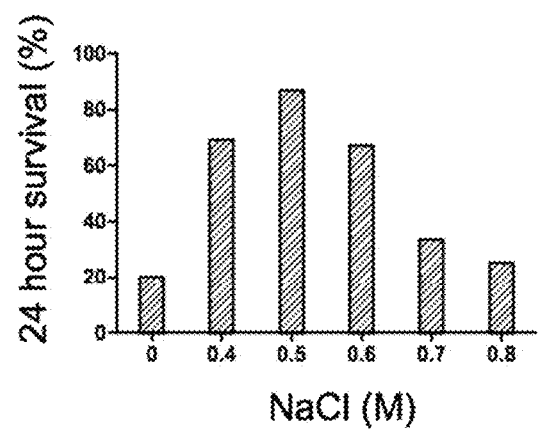

FIG. 11B illustrates graphically that eDIB stability can be screened under a range of environmental conditions enabling rapid characterization.

Figure 11C:
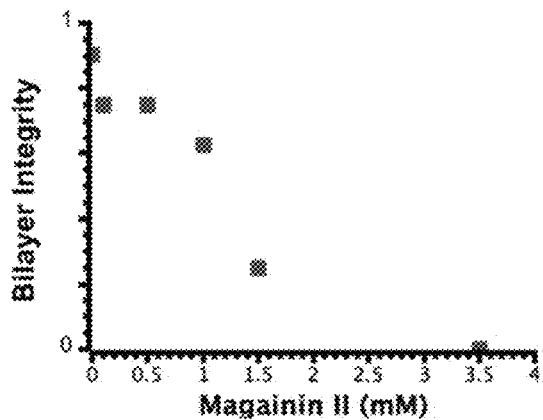

FIG. 11C is a graph of optical characterization of pore forming peptide activity against eDIB membranes where varying concentrations of peptide are added to the external fluid in eDIB containing wells of the 96 well plate.

Figure 11D:
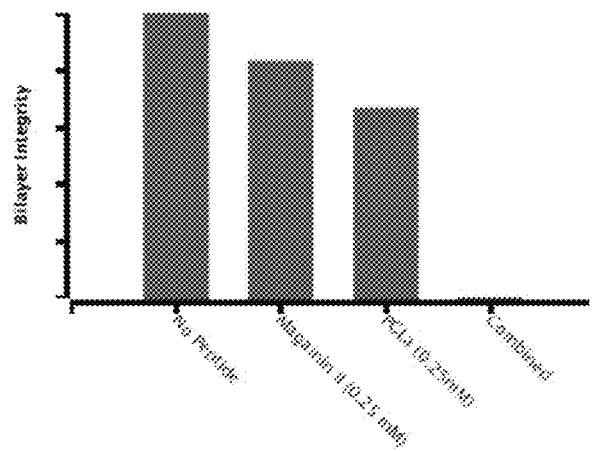

FIG. 11D illustrates that high-density screening enables characterization of a wide parameter space that is challenging by other methods. Results of two-dimensional screen reveal synergistic activity between two membrane pore forming peptides.

DETAILED DESCRIPTION

Materials and Methods

Manufacture of encased Droplet Interface Bilayers (eDIBs)

An example of a process for the creation of eDIBs is outlined in FIG. 2. A hybrid microfluidic device comprising sequential coaxial flow geometries, for the double encapsulation of aqueous droplets, was fabricated by 3D-printing (Ultimaker 2, Ultimaker, Netherlands). An Ethylene tetrafluoroethylene (ETFE) T-junction (ID: 500 μm) was used to produce a regular stream of aqueous droplets (50 mM sodium phosphate) in hexadecane:silicone oil (1:1) with dissolved lipid (DPhPC 5 mg ml−1) (FIG. 2c). FEP tubing (ID: 750 μm) was interfaced with the 3D printed microfluidic device delivering aqueous droplets in a continuous stream of oil. A second input channel in the device received a flow of an aqueous alginate solution (2% w/v with 7.5 mg ml$^{-1}$ suspended $CaCO_3$ microparticles) which was delivered into a hydrophilic surface modified borosilicate glass capillary (ID: 2000 μm) embedded within the 3D printed device. The FEP tubing was mounted such that it terminated within this glass capillary, thereby creating a co-axial flow for droplet generation. This enabled the formation of individual droplets of oil within a continuous alginate flow, with each oil droplet containing a number of internal aqueous droplets (FIG. 2d, 3). The modulation of relative flow rates, of water, oil and alginate, provided control over the number of internal aqueous cores, and the frequency of production. Typically, a flow rate ratio of 0.196:0.196:2.5 ml min$^{-1}$ (aqueous: oil:alginate) was used to generate constructs with 10 internal aqueous compartments. A third fluid input into the 3D printed device received a continuous flow of mineral oil with 0.5% v/v acetic acid. This flowed into a second FEP tube (ID: 2500 μm), within which, the glass capillary carrying the double emulsion of water-droplets-in-oil-in-alginate, was terminated. This second, hydrophobic, coaxial flow geometry, created the triple emulsion, comprising a steady flow of alginate droplets, each containing an internal oil droplet, further encapsulating aqueous droplets (FIG. 2e, 3).

Lipid monolayer self-assembly at the water-oil interfaces, gave rise to bilayers forming between contacting interfaces during the encapsulation process. Alginate gelation and rigidification of the constructs, proceeded in-flow, with the partitioning of acid from the mineral oil into the alginate solution, reducing the pH and liberating calcium from the calcium carbonate to gel the alginate. Constructs were collected on exit from the device. Unlike multisomes, the reported encased structures were freestanding and resistant to rupture on contacting liquid-air or container interfaces. Despite the rigidity, the permeable nature of the alginate shell allows for diffusive access to the encased droplet bilayers.

Surface Modification of Glass Capillaries

Glass capillaries (ID: 2.15 mm OD: 2.8 mm or ID: 2 mm OD: 2.4 mm) to be incorporated into the microfluidic device were sonicated (FB15055, Fisherbrand UK) for 10 minutes in acetone and then methanol and thoroughly dried prior to plasma activation (Diener FEMTO, Germany) using oxygen plasma (0.35 mbar, 15 sccm, 10 minutes). Following plasma activation, activated glass capillaries were soaked overnight in a 2% (v/v) solution of N-(Triethoxysilylpropyl)-O-poly (ethylene oxide) urethane in 2-propanol to render them permanently hydrophilic. Silanised glass capillaries were then rinsed in 2-propanol, dried and cured overnight at 120° C. Successful surface modification was confirmed by contact angle measurement.

Preparation of Fluids

Aqueous inner cores consisted of deionised water with 50 mM sodium dihydrogen phosphate and sulphorhodamine B or lissamine green for colour (50 μM) (pink or blue, respectively). The lipid in oil phase was produced via the evaporation of chloroform containing dissolved DPhPC using a nitrogen gas stream, and by re-dissolving the resultant dry lipid film in a 1:1 mixture of hexadecane and silicone oil AR20 to a final concentration of 5 mg/mL. Alginate solution was prepared by dissolving sodium alginate was stirred at 60° C. for one hour and subsequently sonicated for 1 minute to remove air bubbles. The carrier oil phase was composed of mineral oil with 0.5% glacial acetic acid.

Device Design, Fabrication and Operation

A 3D printed microfluidic device comprising integrated channels interfacing with FEP tubing and glass capillaries was engineered in order to facilitate the production of triple emulsions (water-in-oil-in-water-in-oil) eDIBs as described in the main text and illustrated in FIG. 2. The 3D printed fluidic device and manifold was designed with the aid of CAD software (Solidworks, Dassault Systemes, France) and fabricated by 3D-printing (Ultimaker 2 desktop 3D-printer, Ultimaker, Netherlands) parameterised with CAM slicing software (Cura, Ultimaker, Netherlands). Devices were printed in layers of 50 μm at a print density of 80% using transparent polylactic acid (PLA) filament. FEP tubing (ID: 750 μm and ID: 2500 μm) and glass capillaries were secured in place with epoxy resin to create a leak-free seal. All fluids were delivered by syringe drivers (KD Scientific, World Precision Instruments).

Electrophysiology Experiments eDIBS were placed in a Petri dish within a custom built Faraday cage. Custom Ag/AgCl electrodes were prepared from 100 μm diameter silver wire embedded within a pulled glass capillary (initial internal diameter=1 mm) to provide mechanical stability. The electrode designated for insertion into the internal aqueous cores of the eDIB was sealed with insulatory PDMS except for ~500 μm at the electrode tip. The PDMS was used to insulate from electrical leakage as the electrode was required to pass through the common alginate shell. The second electrode was inserted into the alginate shell. Electrodes were mounted on micromanipulators (Narishige International, USA) and connected to an Axopatch 200B with a 203BU headstage (Molecular Devices, USA). Electrophysiology recordings of bilayer capacitance and ion flux were made respectively under applied potentials of a +/−23 mV triangular wave at 10 Hz or a fixed potential of 10-50 mV.

Data was recorded with WinEDR (University of Strathclyde) analogue filtered at 5 kHz. Electrophysiology traces were digitally filtered post-acquisition with either a 1 kHz or 100 Hz low-pass filter.

Results

Formation of Rigid Encased Droplet Interface Bilayers

Initially, the alginate shell appeared a milky-white colour, due to suspended $CaCO_3$ particles. With progressive acidification of the alginate solution, the capsule became transparent (FIG. 6). In the reported experiments, we used an excess of $CaCO_3$ to achieve rapid initial gelling, thus providing early structural rigidity whilst still in the microfluidic device. Subsequently, the shell became transparent over a period of 1 hour.

The rate of this reaction can be modified to provide control over shell morphology. For example, early gelation was found to produce asymmetric, elongated, ovoid shaped constructs with internal cores often residing at one end, as external rigidity was achieved within the microfluidic channel. Whereas it was found slower gelation gave rise to spherical constructs as greater shell flexibility was maintained under flow conditions until full rigidification was achieved on exit from the device.

Whilst not the subject of detailed study here, we note that control of this gelation may be achieved by modulation of rate and extent of calcium liberation from calcium carbonate. This means that physical parameters such as particle size, concentration, acetic acid concentration, capsule surface area:volume ratio, capsule size and flow conditions (e.g. flow rate dependent advective mixing and oil:alginate volume ratio), can be used to control gelation. A reduction in $CaCO_3$ particle size from ≥30 μm to ≈40-500 nm provided an increase in particle surface area:volume ratio, resulting in more rapid dissolution and progression to transparency. Similarly, buffering conditions of the alginate phase can be used to control the rate and extent of pH change on partitioning of acetic acid to modulate the conditions under which gelation proceeds. In the protein insertion and electrophysiology experiments reported here we employ 0.5× phosphate buffered saline (PBS) in the alginate phase to produce a rugged, yet flexible, outer shell suitable for manual handling and protein diffusion through the hydrogel. After gelation, constructs may be washed in aqueous media to perfuse the gel and enable control of the outershell environment.

Modulation of the buffering capacity of the liquid alginate solution could be used to delay the onset of gelation (FIG. 6). This facilitated off-chip gelation and the formation of spherical constructs unconstrained by micro-fluidic channel geometries. In the reported experiments, in situ acetic acid partitioning from oil to water, was employed to trigger gelation at the point of droplet formation. However, other methods of gelation, such as calcium addition, or the release of photo-caged calcium, could be employed, and the kinetics of calcium delivery may be used to control alginate morphology.

Controlling Contents of eDIB Internal Droplet Network

Substitution of the primary T-junction droplet generating geometry, for a 3D printed device, comprising multiple T-junctions, enabled the generation of alternating sequences of aqueous droplets of different composition (FIG. 2c). These droplets were then subsequently encased to form eDIBs with control over the contents of individual internal compartments, of the droplet network (FIG. 1f). In addition, modulation of the relative fluid flow rates, provided a means to control the number of aqueous droplets encased within each construct. FIG. 4e illustrates one to four internal droplets, with higher numbers illustrated in FIGS. 1 and 3a. The microfluidic method developed here, affords a continuous production method for eDIBs, the reproducibility of which was assessed at a flow rate ratio of 0.196:0.196:2.5:6.67 ml min−1. (aqueous, oil, alginate, oil) Here, eDIBs were produced at a frequency of 2 Hz, with the majority (70%) of constructs containing ten internal, networked aqueous cores, with 96% of constructs containing 10±1 cores. The variability was found to be a consequence of early bilayer formation between contacting aqueous droplets during the encapsulation process. Where this occurred, droplet pairs adjoined by an interface bilayer, were usually either both encased, or both excluded from, the forming droplet, with separation at the bilayer rarely observed. Under continuous operation the device tolerated these fluctuations well, without impacting on subsequent formation events, as might be anticipated owing to the non-linear flow behaviour of multiphase flows.

Generation of Multicellular Integrated eDIB Networks

Further, multiple eDIBs are brought into contact prior to complete gelation to create higher order 2D and 3D eDIB structures, see FIG. 8. Such structures may represent tissue-like materials comprised of individual eDIB cellular units. Similar structures may also be prepared after complete gelation of individual eDIBs with surface forces adhering neighbouring cells. Such arrangements may be separated and reconfigured as desired and can display shape dependent assembly for self-assembly of functional tissue structures.

eDIBs Demonstrate Exceptional Rigidity and Stability

Alginate eDIBs were found to be stable in aqueous, oil and air environments, as well as on solid surfaces including microscope slides, Petri dishes and sample tubes (FIG. 4a-d, 7). The constructs could be ejected directly from the microfluidic device into these environments, or easily manipulated between them, by simply pipetting or tweezing them without damage to the internal droplet network. We have found eDIBs are stable for days to weeks. This ruggedness could enable long-term membrane studies and facilitate otherwise inaccessible combinations of experiments and measurements on individual bilayer constructs. For example, co-incubation of eDIBs with cell culture and extraction followed by microscopy should be possible. Importantly, the ability to easily produce, store and handle constructs enables off-site production and application in a range of environments outside the laboratory. In the course of this work, we would routinely transport eDIB constructs several km between University sites for characterisation.

Alginate eDIBs provide an ideal platform for the application of droplet bilayer networks in a range of previously inaccessible environments, owing to their structural rigidity combined with the permeable properties of the hydrogel shell, and their externally facing bilayers (akin to those of multisomes). This permeability of the protective shell, enables chemical diffusion to the internal constructs, facilitating the possibility of communication between the internal cores of the eDIB, and the wider environment. This is in contrast to previous efforts to stabilise DIBs involving the polymerization of the bulk oil phase to encase droplet bilayer pairs. Whilst this method affords a mechanical scaffold within which the droplet bilayer resides, subsequent access to the bilayer or droplets is not possible.

Pore Insertion in eDIBs Permits Membrane Permeability

The presence of lipid bilayers segregating compartments was confirmed by electrophysiology (FIG. 5a,b). A characteristic square wave current was recorded in response to a triangular wave potential, corresponding to a bilayer capacitance of 2826 pF corresponding to an area of ~0.42 mm2 using previously reported specific bilayer capacitance of 0.652 µF cm−2 for DPhPC. Additionally, transient electroporation of the lipid membranes was observed under an applied potential (+50 mV), giving rise to characteristic transient increases in current corresponding to the formation of electropores.

In subsequent measurements, a 0.2 nL aqueous droplet containing the transmembrane pore forming protein, alpha-hemolysin (α-HL), was contacted with the eDIB. Under an applied potential of 30 mV, successive step-wise increases in current were observed, as the alpha hemolysin diffused through the alginate shell and individual pores spontaneously inserted into the bilayer. This resulted in an ion flux across the membrane (FIG. 5c,d). Two types of insertion events are observed. First, characteristic step increases in current were associated with protein insertion into the bilayer that segregated the electrode within the chosen internal core, from that in the external alginate shell (FIG. 5c inset red pore). Secondly, capacitive transient increases in current were observed that subsequently decayed (FIG. 5c blue trace). Such behaviour has previously been reported where pore insertion into indirectly linked bi-layers within a droplet bilayer network, resulted in a transient increase in current. Consequently, we attribute this behaviour to insertions into neighbouring bilayers of the connected network (FIG. 5c inset blue network). Since pore insertion is a stochastic process, we observed a combination of these events with α-HL pores inserting into a number of accessible, externally facing, bilayers of the network. This results in a mixture of the two observed behaviours. At higher protein concentration, successive step-wise increases in current with a broadening of conductance levels is seen, attributable to successive individual conductive insertions into the interrogated bilayer together with simultaneous capacitive insertions also taking place (FIG. 5c). These experiments demonstrate the formation of bilayers within the eDIB constructs and the ability of the internal droplets to communicate with the external environment, by the diffusion of functional protein through the alginate shell to the membrane, and subsequent ionic exchange between the internal cores and external environment.

These experiments demonstrate the formation of bilayers within the eDIB constructs, and the ability for the internal droplets to communicate with the external environment by the diffusion of functional protein through the alginate shell to the membrane, and subsequent ionic exchange between the internal cores and external environment.

SUMMARY

Here, we have shown that encased droplet networks represent a highly robust artificial bilayer platform with the ability to interface with the external surroundings. eDIBs are able to withstand manual and mechanical handling and are stable for prolonged periods and in a range of environments. We have demonstrated that microfluidic manufacture provides a means to control both internal droplet number and contents, and offers scalable production. This control enables eDIBs to retain the favorable properties of DIBs, such as (i) the asymmetry of droplet contents or bilayer lipid composition, (ii) the insertion of functional membrane proteins, and (iii) the chemical communication between droplets, but whilst affording far superior mechanical stability and environmental compatibility. This development provides the opportunity to widen the use of artificial lipid bilayers for fundamental science, and also to harness the enormous potential of DIBs and droplet networks for use outside of the laboratory, enabling their application as functional materials for interfacing with the external world. eDIBs could fulfil a similar role as synthetic organoids or as diagnostic or therapeutic platforms capable of dynamic interaction with their surroundings. We propose that such constructs will have use beyond healthcare with the opportunity to create lab-in-a-capsule technology in compartmentalised eDIBs. These could represent self-contained assay platforms for use in complex environments that are not readily reduced to the laboratory setting. Their mass production by microfluidics could enable them to be used as units of complex composition in higher-order structures, forming synthetic tissues that are readily compatible with a wide range of environments.

The invention claimed is:

1. An isolatable and manipulatable artificial cell system comprising: at least one hydrophilic/polar droplet constrained within an amphiphilic monolayer and contained within an oil droplet which is in turn contained within an amphiphilic monolayer encased within a hydrophilic shell to provide at least one droplet-interface bilayer (DIB) wherein said hydrophilic shell is a hydrogel polymer shell that forms a discrete case about said cell system which is at least semi-rigid and which is capable, under suitable conditions, of undergoing polymerization/depolymerisation.

2. The artificial cell system according to claim 1 wherein the DIB comprises amphipathic molecules that are either naturally occurring and/or synthetic.

3. The artificial cell system according to claim 1 wherein said DIB contains either a single type of polar liquid or two different types.

4. The artificial cell system according to claim 1 wherein said DIB comprises an additional constituent selected from the group comprising: a membrane protein, a structural protein, an enzyme, selective/non-selective membrane transport protein, an ion channel, a pore forming protein, a peptide, DNA, RNA, cells, a polymer, a biological molecule, liquid crystals, an organic or inorganic molecule, or nanoparticles.

5. The artificial cell system according to claim 4 wherein said DIB comprises more than one of said constituents of a known biological pathway or a synthetic pathway.

6. The artificial cell system according to claim 1 wherein said shell is at least semi-permeable, so as to permit communication with its external environment.

7. The artificial cell system according to claim 1 wherein said shell further comprises at least one environmentally responsive element or material whereby a change in the properties of the shell can be induced by application of an appropriate stimuli to the shell.

8. The artificial cell system according to claim 1 wherein said shell is selected from the group comprising or consisting of: agarose, chitosan, and alginate.

9. A liquid suspension comprising a liquid in which there is provided a plurality of artificial cell systems according to claim 1.

10. A structure comprising a plurality of artificial cell systems according to claim 1 wherein at least two of said artificial cell systems are in contact with each other.

* * * * *